(12) United States Patent
Iguchi et al.

(10) Patent No.: US 9,096,894 B2
(45) Date of Patent: Aug. 4, 2015

(54) DRY REAGENT, DRY REAGENT KIT, REAGENT CONTAINER, AND METHOD FOR PRODUCING DRY REAGENT

(75) Inventors: Aki Iguchi, Kyoto (JP); Mariko Komori, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 300 days.

(21) Appl. No.: 13/482,380

(22) Filed: May 29, 2012

(65) Prior Publication Data

US 2012/0301943 A1 Nov. 29, 2012

(30) Foreign Application Priority Data

May 26, 2011 (JP) .................................. 2011-118378
May 24, 2012 (JP) .................................. 2012-118521

(51) Int. Cl.
*C12Q 1/68* (2006.01)
(52) U.S. Cl.
CPC ................... *C12Q 1/6846* (2013.01)
(58) Field of Classification Search
None
See application file for complete search history.

(56) References Cited

U.S. PATENT DOCUMENTS

| | | | | |
|---|---|---|---|---|
| 5,380,489 | A | * | 1/1995 | Sutton et al. ................. 422/68.1 |
| 5,565,318 | A | | 10/1996 | Walker et al. |
| 6,140,110 | A | | 10/2000 | Vinayagamoorthy et al. |
| 2007/0243601 | A1 | * | 10/2007 | Korpimaki et al. ........ 435/287.9 |
| 2008/0268434 | A1 | | 10/2008 | Nurmi et al. |
| 2010/0136542 | A1 | | 6/2010 | Lee et al. |

FOREIGN PATENT DOCUMENTS

| | | |
|---|---|---|
| JP | 2007-043997 A | 2/2007 |
| JP | 2008-601331 A | 1/2008 |
| WO | 2005/118144 A1 | 12/2005 |
| WO | 2005/118849 A1 | 12/2005 |
| WO | 2007/005626 A1 | 1/2007 |
| WO | 2012/010708 A1 | 1/2012 |

OTHER PUBLICATIONS

Hot Master manual (5 Prime, 2007, p. 1-12).*
Search Report issued in corresponding European Patent Application No. 12169615.7 dated Aug. 16, 2012.
Anonymous, "Red Load Tag Master Lyophilisate/high yield," Jun. 3, 2009, www.jenabioscience.com/images/dded44ba94/PCR-154.pdf.
Anonymous, "Taq Pol/high yield buffer," Jun. 3, 2009, www.jenabioscience.com/images/dded44ba94/PCR-201.pdf.
Anonymous, "PCR applications manual", 3rd edition, 2006, www.roche-applied-science.com/publications/print_mat/per_application_manual_3rd_edition.pdf.
Office Action issued in corresponding European Patent Application No. 12169615.7 dated Aug. 1, 2013.
"Herculase II Fusion DNA Polymerase," catalog #600675, Agilent, 2011, Retrieved from the Internet, URL: http://www.chem.agilent.comilibrary/usermanuals/Public/600675.pdf (retrieved on Jul. 25, 2013).
Office Action issued in corresponding European Patent Application No. 12169615.7 dated Nov. 3, 2014.

* cited by examiner

Primary Examiner — Stephanie K Mummert
(74) Attorney, Agent, or Firm — Morgan, Lewis & Bockius LLP (57) ABSTRACT

The present invention provides a dry reagent capable of amplifying a nucleic acid even after being stored in a dry state at room temperature, a dry reagent kit, a reagent container, and a method for producing the dry reagent and methods of producing and using thereof.

12 Claims, 1 Drawing Sheet

SEQUENCE LISTING

<160> NUMBER OF SEQ ID NOS: 3

<210> SEQ ID NO 1
<211> LENGTH: 18
<212> TYPE: DNA
<213> ORGANISM: Artificial
<220> FEATURE:
<223> OTHER INFORMATION: probe

<400> SEQUENCE: 1
ggagaaggtc aaggtatc                                                 18

```
<210> SEQ ID NO 2
<211> LENGTH: 18
<212> TYPE: DNA
<213> ORGANISM: Artificial
<220> FEATURE:
<223> OTHER INFORMATION: forward primer

<400> SEQUENCE: 2
cggagcccct gcatgcaa                                                      18

<210> SEQ ID NO 3
<211> LENGTH: 29
<212> TYPE: DNA
<213> ORGANISM: Artificial
<220> FEATURE:
<223> OTHER INFORMATION: reverse primer

<400> SEQUENCE: 3
aatgatacta tgaatttggg gacttcgaa                                          29
```

DRY REAGENT, DRY REAGENT KIT, REAGENT CONTAINER, AND METHOD FOR PRODUCING DRY REAGENT

CROSS-REFERENCE TO RELATED APPLICATION

This application claims priority from Japanese Patent Application Nos. 2011-118378, and 2012-118521, filed on May 26, 2011 and May 24, 2012. The entire subject matter of these Japanese Patent Applications is incorporated herein by reference.

SEQUENCE LISTING SUBMISSION VIA EFS-WEB

A computer readable text file, entitled "SequenceListing.txt," created on or about May 26, 2012 with a file size of about 4 kb contains the sequence listing for this application and is hereby incorporated by reference in its entirety.

BACKGROUND OF THE INVENTION

The present disclosure relates to a dry reagent, a dry reagent kit, a reagent container, and a method for producing the same.

In the field of molecular biology, various nucleic acid amplification methods such as the PCR method and the like are widely used as a method for amplifying a target nucleic acid sequence. The nucleic acid amplification is performed in a reaction solution containing, as essential components, polymerase, nucleic acid monomers such as dNTPs, an inorganic salt, a primer, and a buffer agent such as trishydroxyaminomethane (formal name: tris(hydroxymethyl)aminomethane). In this nucleic acid amplification reaction, a commercially available kit for nucleic acid amplification is generally used. The kit may be, for example, a kit including multiple liquid reagents obtained by combining the essential components and stored in the respective containers. However, there is a problem in that it is difficult to store the liquid reagents at normal temperature for a long period of time because the stability thereof is poor.

In order to avoid the stability problem, a kit for nucleic acid amplification, obtained by combining a dry reagent containing a nucleic acid monomer and a primer as some of essential components and a liquid reagent containing the other essential components has been proposed (JP 2007-43997 A). According to this kit, for example, a nucleic acid may be amplified by adding a test sample to the dry reagent so as to dissolve the dry reagent in the test sample and thereafter mixing a liquid reagent in the mixture thus obtained. However, it is difficult to store the liquid reagent at normal (room) temperature because the stability of polymerase contained in the liquid reagent is poor when in a liquid. Therefore, it is necessary to refrigerate or freeze the liquid reagent, for example. However, for example, in view of the case of subjecting a large number of test samples to nucleic acid amplification and distributing the liquid reagents, it is desired that the kit for nucleic acid amplification may be stored at normal (room) temperature.

On the other hand, as a kit for nucleic acid amplification, including essential components in a dry state, a kit including a dry reagent containing polymerase and a dry reagent containing essential components other than polymerase individually has been proposed (JP 2008-501331 A).

BRIEF SUMMARY OF THE INVENTION

However, the inventors of the present invention found as the result of storing a dry reagent containing essential components other than polymerase, that specifically, the stability of a nucleic acid monomer after storage was significantly reduced, so that it was difficult to sufficiently amplify a nucleic acid.

Hence, the present invention is intended to provide a dry reagent capable of being used in the amplification of a nucleic acid even after being stored in a dry state at room temperature, for example, a dry reagent kit, a reagent container, and a method for producing the dry reagent.

In order to achieve the aforementioned object, the present invention is intended to provide a dry reagent for use in nucleic acid amplification, the dry reagent containing: at least one type of nucleic acid monomer; and $Mg^{2+}$, wherein the molar ratio between the at least one type of nucleic acid monomer and the $Mg^{2+}$ is from 1:0.03 to 1:100. The present invention also provides a dry reagent kit for use in nucleic acid amplification, the dry reagent kit including the dry reagent of the present invention, a reagent container for use in nucleic acid amplification, the reagent container containing: a base (base material, e.g. a surface); and the dry reagent of the present invention, wherein the dry reagent is placed in the base (e.g. on the surface). The present invention also extends to use of the dry reagent, dry reagent kit or reagent container, as described herein, in nucleic acid amplification.

The present invention also provides a method for producing a dry reagent for use in nucleic acid amplification, the method including: the step of drying a liquid reagent containing at least one type of nucleic acid monomer and $Mg^{2+}$, wherein the molar ratio between the at least one type of nucleic acid monomer and the $Mg^{2+}$ in the liquid reagent is from 1:0.03 to 1:100.

According to the dry reagent of the present invention, a nucleic acid may be amplified even after storing the dry reagent at room temperature, for example. Therefore, for example, the handling of the dry reagent becomes really easy when a large number of test samples are subjected to nucleic acid amplification, and the dry reagents are distributed. Thus, it becomes possible to reduce the cost involved therein. Moreover, the dry reagent may be stored in a dry state. Therefore, for example, it becomes possible to make a chip by placing all of the essential components on a chip. As described above, the dry reagent of the present invention may maintain the ability to amplify a nucleic acid even after being stored, and the handling of the dry reagent is improved. Thus, the dry reagent of the present invention may be a useful tool in gene analysis utilizing nucleic acid amplification and the like.

BRIEF DESCRIPTION OF THE DRAWINGS

FIG. 1 shows graphs each illustrating the result of Tm analysis of a reaction solution according to Examples 1A and 2A, each indicating the relationship between the amount of change in fluorescence intensity of BODIPY FL per unit time (d (fluorescence intensity increase amount)/dt) and the temperature. The vertical axis indicates the amount of change in fluorescence intensity per unit time (d (fluorescence intensity increase amount)/dt), and the horizontal axis indicates the temperature (° C.).

DETAILED DESCRIPTION OF THE INVENTION

<Dry Reagent>

The dry reagent of the present invention is, as mentioned above, a dry reagent for use in nucleic acid amplification, the dry reagent containing: at least one type of nucleic acid monomer; and $Mg^{2+}$, wherein the molar ratio between the at least one type of nucleic acid monomer and the $Mg^{2+}$ is from 1:0.03 to 1:100. In the present invention, the molar ratio between the nucleic acid monomer and the $Mg^{2+}$ is, for example, the molar ratio of the $Mg^{2+}$ to the at least one type of nucleic acid monomer having a base. Hereinafter, the molar ratio between the nucleic acid monomer (s) and the $Mg^{2+}$ is indicated as the molar ratio (s:$Mg^{2+}$), and the condition that the molar ratio falls within the above-described range also is referred to as the condition sM.

In the dry reagent of the present invention, the molar ratio (s:$Mg^2$) is such that: the lower limit thereof may be 1:0.03, 1:1; the upper limit thereof may be 1:100, 1:50, 1:30, 1:20, 1:15, or 1:10; and the range thereof may be from 1:0.03 to 1:100, from 1:0.03 to 1:50, or from 1:1 to 1:30.

The dry reagent of the present invention may contain two or more types of nucleic acid monomers, three or more types of nucleic acid monomers, four or more types of nucleic acid monomers, or four or five types of nucleic acid monomers. When the dry reagent contains two or more types of nucleic acid monomers, it is only necessary that, as described above, the molar ratio (s:$Mg^2$) between at least one type of nucleic acid monomer and $Mg^{2+}$ satisfies the range of the condition sM (1:0.03 to 1:100). For example, the molar ratio between each of two types of nucleic acid monomers and $Mg^{2+}$ may satisfy the above range, or the molar ratio between each of three, four, or five types of nucleic acid monomers and $Mg^{2+}$ may satisfy the above range.

Examples of the base of the nucleic acid monomer in the present invention include A (adenine), G (guanine), C (cytosine), T (thymine), and U (uracil), which are the typical bases constituting nucleic acid (DNA or RNA). Hereinafter, a nucleic acid monomer having adenine is referred to as an adenine nucleic acid monomer, a nucleic acid monomer having guanine is referred to as a guanine nucleic acid monomer, a nucleic acid monomer having cytosine is referred to as a cytosine nucleic acid monomer, a nucleic acid monomer having thymine is referred to as a thymine nucleic acid monomer, and a nucleic acid monomer having uracil is referred to as an uracil nucleic acid monomer. Examples of the nucleic acid monomer having a base include nucleotides such as adenine nucleotide, guanine nucleotide, cytosine nucleotide, thymine nucleotide, and uracil nucleotide, and specific examples thereof include deoxyribonucleotide triphosphates (dNTP) such as dATP, dGTP, dCTP, dTTP, and dUTP. Other examples of the base include bases that may serve as substrates for polymerases, and specific examples thereof include inosine. The nucleic acid monomer may be a natural nucleotide (deoxyribonucleotide, ribonucleotide), or an artificial nucleotide, for example. Examples of the artificial nucleotide include bridged nucleic acids and peptide nucleic acids.

In the following, embodiments of the present invention where the dry reagent contains, as the at least one type of nucleic acid monomer, an adenine nucleic acid monomer (e.g., dATP), a guanine nucleic acid monomer (e.g., dGTP), a cytosine nucleic acid monomer (e.g., dCTP), and a thymine nucleic acid monomer (e.g., dTTP), and/or uracil nucleic acid monomer (e.g., dUTP) will be illustrated as appropriate. It is to be noted, however, that the present invention is by no means limited thereto.

In the present invention, the molar ratio (ratio) of each type of nucleic acid monomer may be determined individually. For example, it may be determined with reference to the amount of each type of nucleic acid monomer. The amount is, for example, the number of moles, the concentration, or the like. The concentration is, for example, the concentration of each type of nucleic acid monomer in the reagent before being dried in the preparation of the dry reagent. In the dry reagent, the number of moles of each type of nucleic acid monomer in the reagent after being dried reflects the number of moles of the same in the reagent before being dried. Specifically, when the dry reagent of the present invention contains an adenine nucleic acid monomer (e.g., dATP), a guanine nucleic acid monomer (e.g., dGTP), a cytosine nucleic acid monomer (e.g., dCTP), and a thymine nucleic acid monomer (e.g., dTTP), and/or uracil nucleic acid monomer (e.g., dUTP), the molar ratio of each type of nucleic acid monomer may be determined with reference to the amount thereof.

Specifically, when the dry reagent of the present invention contains, for example, an adenine nucleic acid monomer, a guanine nucleic acid monomer, a cytosine nucleic acid monomer, and a thymine nucleic acid monomer, it is only necessary that the molar ratio (s:$Mg^2$) between at least one out of these four types of nucleic acid monomers and $Mg^{2+}$ is in the range of the condition sM (1:0.03 to 1:100). In some embodiments, the molar ratio between each of two types of nucleic acid monomers and $Mg^{2+}$ is in the above range. In additional embodiments, the molar ratio between each of three types of nucleic acid monomers and $Mg^{2+}$ is in the above range. In yet additional embodiments, the molar ratio between each of four types of nucleic acid monomers and $Mg^{2+}$ is in the above range. In further embodiments, the molar ratio between each of the adenine nucleic acid monomer, the guanine nucleic acid monomer, and the cytosine nucleic acid monomer and $Mg^{2+}$ is in the above range, or in addition to the above molar ratios, the molar ratio between the thymine nucleic acid monomer and $Mg^{2+}$ also may be in the above range.

Furthermore, the dry reagent of the present invention may contain a uracil nucleic acid monomer instead of a thymine nucleic acid monomer, for example. When a uracil nucleic acid monomer is used, it is known that the concentration thereof generally is set to be higher than those of the other nucleic acid monomers, i.e., the adenine nucleic acid monomer, the guanine nucleic acid monomer, and/or the cytosine nucleic acid monomer (e.g., see page 109 of PCR Applications Manual $3^{rd}$ edition, Roche Applied Science). When the dry reagent of the present invention contains a uracil nucleic acid monomer, the following condition may be given as an example of the number of moles thereof, for example. The ratio between the average number of moles calculated from the number of moles of the nucleic acid monomer having adenine, the nucleic acid monomer having guanine, and the nucleic acid monomer having cytosine and the number of moles of the nucleic acid monomer having uracil is such that: the lower limit thereof is, for example, 1:0.5, 1:1, or 1:2; the upper limit thereof may be, for example, 1:10, 1:6, or 1:4; and the range thereof may be, for example, from 1:0.5 to 1:10, 1:1 to 1:6, or from 1:2 to 1:4.

When the dry reagent of the present invention contains, for example, an adenine nucleic acid monomer, a guanine nucleic acid monomer, a cytosine nucleic acid monomer, and a uracil nucleic acid monomer, it is only necessary that the molar ratio (s:$Mg^2$) between at least one out of these four types of nucleic acid monomers and $Mg^{2+}$ is in the range of the condition sM (1:0.03 to 1:100). In some embodiments, the molar ratio between each of two types of nucleic acid monomers and $Mg^{2+}$ is in the above range. In additional embodiments, the molar ratio between each of three or four types of nucleic acid monomers and $Mg^{2+}$ is in the above range. In yet additional embodiments, the molar ratio between each of the adenine nucleic acid monomer, the guanine nucleic acid monomer, and the cytosine nucleic acid monomer and $Mg^{2+}$ is in the above range. In this case, the molar ratio between the uracil nucleic acid monomer and $Mg^{2+}$ may satisfy the range of the condition sM, or may not satisfy the range of the condition sM, for example. In the latter case, the molar ratio (s:$Mg^2$) between the uracil nucleic acid monomer and $Mg^{2+}$ is such that, for example: the lower limit thereof may be, for example, 1:0.003, 1:0.0075, 1:0.01, 1:0.075, or 1:0.25; the upper limit may be, for example, 1:200, 1:50, 1:25, or 1:15; and the range thereof may be, for example, from 1:0.003 to 1:200, from 1:0.0075 to 1:50, from 1:0.01 to 1:50, from 1:0.075 to 1:50, from 1:0.075 to 1:25 or 1:0.01 to 1:25, or from 1:0.25 to 1:15.

In the present invention, the molar ratio between the total number of moles of all nucleic acid monomers contained in the dry reagent and the number of moles of $Mg^{2+}$ is 1:0.03 to 1:100, for example. Hereinafter, the ratio between the total number of moles (t) of all the nucleic acid monomers and the number of moles of $Mg^{2+}$ is indicated as the molar ratio (t:$Mg^2$), and the condition that the molar ratio falls within the above numerical range also is referred to as the condition tM.

In the dry reagent of the present invention, the molar ratio (t:$Mg^2$) is such that: the lower limit thereof may be, for example, 1:0.0075, 1:0.01, 1:0.075, 1:0.1, or 1:0.2; the upper limit thereof may be, for example, 1:25, 1:20, 1:10, or 1:6; and the range thereof may be, for example, from 1:0.0075 to 1:25, from 1:0.0075 to 1:20, 1:0.1 to 1:10, or 1:0.2 to 1:6.

The molar ratio (t:$Mg^2$) is the ratio between the number of moles of the total amount (the total number of moles) of the respective types of nucleic acid monomers contained in the dry reagent and the number of moles of $Mg^{2+}$. The total amount of the nucleic acid monomers in the dry reagent is, in other words, a perception that, the respective types of nucleic acid monomers contained in the dry reagent as a whole are considered as a single nucleic acid monomer, and the total amount thereof is determined. In this case, the ratios between the respective types of nucleic acid monomer in the dry reagent may or may not be uniform, for example.

When a uracil nucleic acid monomer is used, the concentration thereof generally is set to be higher than those of the other nucleic acid monomers, i.e., the adenine nucleic acid monomer, the guanine nucleic acid monomer, and/or the cytosine nucleic acid monomer, as described above. When the dry reagent of the present invention contains a uracil nucleic acid monomer, the molar ratio (t:$Mg^{2+}$) may be such that the value obtained based on the total number of moles of all the nucleic acid monomers satisfies the condition tM (1:0.03 to 1:100), or the value obtained by the following calculation method satisfies the condition tM (1:0.03 to 1:100). The calculation method in the latter case may be employed when, for example, the number of moles of the uracil nucleic acid monomer is greater than those of the other nucleic acid monomers. The calculation method specifically is as follows. First, the average number of moles of the nucleic acid monomers other than the uracil nucleic acid monomer is assumed to be the number of moles of the uracil nucleic acid monomer. The sum of the assumed number of moles of the uracil nucleic acid monomer and the number of moles of the respective types of other nucleic acid monomers is determined as the assumed total number of moles of all the nucleic acid monomers. Then, the molar ratio (t:$Mg^{2+}$) is calculated from the assumed total number of moles and the number of moles of $Mg^{2+}$. This value may satisfy the condition tM.

In the present invention, the dry reagent is also referred to as a "solid reagent" or a "nucleic acid monomer dry reagent", for example. The drying method at the time of producing the dry reagent is not particularly limited and may be, for example, freeze-drying, spin drying, vacuum drying, hot-air drying, natural drying, or the like. The natural drying does not require any equipment and the like, so that the labour and cost may be reduced, for example.

In the present invention, each of a nucleic acid monomer, $Mg^{2+}$, $K^+$, polymerase, trishydroxyaminomethane (formal name: tris(hydroxymethyl)aminomethane, also referred to as "Tris" hereinafter), and a primer is referred to as an "essential component for nucleic acid amplification". It is to be noted that each of these components is an essential component for nucleic acid amplification, which does not mean the dry reagent of the present invention contains all of these essential components.

Specific examples of the dry reagent of the present invention include a first nucleic acid monomer dry reagent containing no $K^+$ and a second nucleic acid monomer dry reagent containing $K^+$ as mentioned below. Regarding the explanation etc. of the number of moles and the molar ratio, the above description may be referred to, unless otherwise stated.

The first nucleic acid monomer dry reagent of the present invention contains: at least one type of nucleic acid monomer; and $Mg^{2+}$ and contains no $K^+$, and the molar ratio (s:$Mg^{2+}$) between the at least one type of nucleic acid monomer (s) and the $Mg^{2+}$ is from 1:0.3 to 1:100. In the first nucleic acid monomer dry reagent, the condition sM of the molar ratio (s:$Mg^{2+}$) between the nucleic acid monomer (s) and $Mg^{2+}$ is such that: the lower limit thereof may be 1:0.3, 1:0.5, or 1:1; the upper limit thereof may be 1:100, 1:50, 1:30, 1:20, 1:15, or 1:10; and the range thereof may be, as mentioned above, from 1:0.3 to 1:100, from 1:0.5 to 1:50, or from 1:1 to 1:30. It is generally known that the nucleic acid amplification reaction may be inhibited when an excess amount of $Mg^{2+}$ is added to a reagent for nucleic acid amplification (see page 18 of roche-applied-science.com/PROD_INF/MANUALS/per_man/chapter_2.pdf). Therefore, the maximum of the molar ratio (s:$Mg^{2+}$) between the nucleic acid monomer (s) and the $Mg^{2+}$ is about 1:100, for example.

The type of the nucleic acid monomer contained in the first nucleic acid monomer dry reagent is not particularly limited, and is as described above, for example. When the first nucleic acid monomer dry reagent contains two or more types of nucleic acid monomers, it is only necessary that, as described above, the molar ratio (s:$Mg^{2+}$) between at least one type of nucleic acid monomer and $Mg^{2+}$ satisfies the above range. For example, the molar ratio between each of the two types of nucleic acid monomers and $Mg^{2+}$ may satisfy the above range, or the molar ratio between each of three, four, or five types of nucleic acid monomers and $Mg^{2+}$ may satisfy the above range.

In the first nucleic acid monomer dry reagent, the molar ratio (t:$Mg^{2+}$) between the total number of moles (t) of all the nucleic acid monomers and the number of moles of $Mg^{2+}$ is such that: the lower limit thereof may be, for example, 1:0.075, 1:0.1, or 1:0.2; the upper limit thereof may be, for example, 1:25, 1:20, 1:10, or 1:6; and the range thereof may be, for example, from 1:0.075 to 1:25, from 1:0.075 to 1:20, from 1:0.1 to 1:10, or from 1:0.2 to 1:6.

The first nucleic acid monomer dry reagent may contain $Mg^{2+}$ in the state of being ions or a salt, for example. Examples of the salt of $Mg^{2+}$ include $MgCl_2$, $Mg(CH_3COO)_2$, $MgBr_2$, $MgSO_4$, and $Mg(NO_3)_2$.

The first nucleic acid monomer dry reagent may further contain, in addition to the nucleic acid monomer and $Mg^{2+}$, an optional additional component other than the polymerase, the primer, and $K^+$. Examples of the optional additional component include a surfactant, a sugar, and a polymer.

Although the first nucleic acid monomer dry reagent may further contain Tris, for example, may not contain Tris. In the case where the first nucleic acid monomer dry reagent contains Tris, the condition sT of the molar ratio (s:Tris) between the at least one type of nucleic acid monomer (s) and Tris is, for example, 60 parts or less of Tris to 1 part of the nucleic acid monomer (1:60 or less), 1:30 or less, 1:20 or less, or 1:15 or less, 1:10 or less, or 1:1 or less.

In the first nucleic acid monomer dry reagent, the condition tT of the molar ratio (t:Tris) between the total number of moles (t) of all the nucleic acid monomers and the number of moles of Tris is, for example, 15 parts or less of Tris to 1 part of all the nucleic acid monomers (1:15 or less), 1:6 or less, or 1:4 or less. The total number of moles of all the nucleic acid monomers may be set in the same manner as described above.

When the first nucleic acid monomer dry reagent contains two or more types of nucleic acid monomers, as described above, the molar ratio (s:Tris) between at least one type of nucleic acid monomer (s) and the Tris may satisfy the range of the condition sT. In some embodiments, the molar ratio between each of two types of nucleic acid monomers and the Tris may satisfy the above range. In additional embodiments, the molar ratio between each of three, four, or five types of nucleic acid monomers and the Tris may satisfy the above range.

The amounts of the nucleic acid monomer, $Mg^{2+}$, and the optional additional component, contained in the first nucleic acid monomer dry reagent are not particularly limited. Each of the amounts may be, for example, the amount required for a single nucleic acid amplification or multiple nucleic acid amplifications. In the former case, for example, the first nucleic acid monomer dry reagent is mixed in a solvent as appropriate when used, and the whole mixture thus obtained is used in nucleic acid amplification. In the latter case, for example, the first nucleic acid monomer dry reagent is mixed in a solvent as appropriate when used, the amount required for nucleic acid amplification is taken from the mixture thus obtained and used.

When a nucleic acid is amplified, components other than the components contained in the first nucleic acid monomer dry reagent among the above-mentioned "essential components for nucleic acid amplification" may be contained in, for example, the following dry reagent (A) and/or dry reagent (B):

(A) a dry reagent containing polymerase and containing no $Mg^{2+}$, $K^+$, Tris, a nucleic acid monomer, and a primer; and
(B) a dry reagent containing a primer and containing no $K^+$.

Hereinafter, the dry reagent (A) is also referred to as a "polymerase dry reagent", and the dry reagent (B) is also referred to as a "primer dry reagent". The dry reagent (A) and the dry reagent (B) are individual dry reagents that are different from the first nucleic acid monomer dry reagent.

When a nucleic acid is amplified using the first nucleic acid monomer dry reagent, the reagent to be used in combination with the first nucleic acid monomer dry reagent is not particularly limited, and for example, the polymerase dry reagent (A) and/or primer dry reagent (B) may be used. For example, either one or both of the polymerase dry reagent (A) and the primer dry reagent (B) may be used in combination with the first nucleic acid monomer dry reagent. In the case of using either one of them in combination with the first nucleic acid monomer dry reagent, a nucleic acid amplification reaction may be performed further using a liquid reagent in combination, for example. In some embodiments, the liquid reagent may contain components other than the components contained in the first nucleic acid monomer dry reagent and the dry reagent (A) or (B) among the essential components for nucleic acid amplification. In this case, an amplification reaction may be performed by dissolving the above-described various dry reagents in the liquid reagent or a test sample when the dry reagents are used, for example. On the other hand, in the case of using both of them in combination with the first nucleic acid monomer dry reagent, an amplification reaction may be performed by dissolving these dry reagents in a solvent or a test sample, for example. The solvent is not particularly limited, and for example, water, a buffer solution, or the like may be used. The test sample is not particularly limited and may be a liquid containing a template for nucleic acid amplification.

The polymerase dry reagent (A) may further contain, in addition to the polymerase, an optional additional component other than $Mg^{2+}$, $K^+$, Tris, the nucleic acid monomer, and the primer. Examples of the optional additional component include an enzyme stabilizing agent, a surfactant, a sugar, and a polymer. The primer dry reagent (B) may further contain, in addition to the primer, an optional additional component other than $K^+$. Examples of the optional additional component include an enzyme stabilizing agent, a surfactant, a sugar, and a polymer.

A method for producing the first nucleic acid monomer dry reagent is not particularly limited, and for example, it may be produced by drying a first liquid reagent containing the at least one type of nucleic acid monomer and $Mg^{2+}$.

The first liquid reagent may be prepared according to the types and ratio of components to be contained in the first nucleic acid monomer dry reagent, for example. The molar ratio (s:$Mg^{2+}$) between the at least one type of nucleic acid monomer (s) and the $Mg^{2+}$ in the first liquid reagent is the same as mentioned above. Also, the molar ratio between the total number of moles of all the nucleic acid monomers and $Mg^{2+}$ is as described above, for example.

The first liquid reagent may further contain the above-mentioned optional additional component, for example. The first liquid reagent may contain no Tris, for example. In the case where the first liquid reagent contains Tris, the molar ratio (s:Tris) between the nucleic acid monomer (s) and the Tris is the same as mentioned above, for example. Also, the molar ratio between the total number of moles of all the nucleic acid monomers and $Mg^{2+}$ is as described above, for example.

The first liquid reagent may be prepared by dissolving or dispersing the above-mentioned various components in a solvent, for example. The solvent is not particularly limited and may be, for example, water.

Next, the second nucleic acid monomer dry reagent of the present invention contains at least one type of nucleic acid monomer and $Mg^{2+}$, and further contains $K^+$. In the second nucleic acid monomer dry reagent, the condition sM of the molar ratio (s:$Mg^2$) between the nucleic acid monomer (s) and $Mg^{2+}$ is 1:0.03 to 1:100. The molar ratio (s:$Mg^{2+}$) is such that: the lower limit thereof may be 1:0.03, 1:0.1, 1:0.3, 1:0.5, or 1:1; the upper limit thereof may be 1:100, 1:50, 1:30, 1:20, 1:15, or 1:10; and the range thereof may be 1:0.03 to 1:100, 1:0.03 to 1:50, 1:0.3 to 1:50, 1:0.3 to 1:30, 1:1 to 1:50, 1:1 to 1:30, or 1:1 to 1:30.

In the second nucleic acid monomer dry reagent, the condition sK of the molar ratio (s:$K^+$) between the nucleic acid monomer (s) and $K^+$ is not particularly limited. The molar ratio (s:$K^+$) is such that: the lower limit thereof may be, for example, 1:0.01, 1:0.03, 1:0.1, or 1:1; the upper limit thereof may be, for example, 1:1000, 1:500, 1:300 or 1:100; and the range thereof may be, for example, from 1:0.01 to 1:1000, from 1:0.03 to 1:1000, from 1:0.1 to 1:500, or from 1:1 to 1:300.

The type of the nucleic acid monomer contained in the second nucleic acid monomer dry reagent is not particularly limited, and is as described above, for example. When the second nucleic acid monomer dry reagent contains two or more types of nucleic acid monomers, it is only necessary that, as described above, the molar ratio (s:$Mg^{2+}$) of $Mg^{2+}$ and the molar ratio (s:$K^+$) of $K^+$ to the at least one type of nucleic acid monomer satisfy the ranges of the conditions sM and sK, respectively. For example, the molar ratios of $Mg^{2+}$ and $K^+$ to each of two types of nucleic acid monomers may satisfy the above ranges, respectively. In some embodiments, the molar ratios of $Mg^{2+}$ and $K^+$ to each of three, four, or five types of nucleic acid monomers may satisfy the above ranges, respectively.

In the second nucleic acid monomer dry reagent, the condition tM of the molar ratio (t:$Mg^2$) between the total number of moles (t) of all the nucleic acid monomers and the number of moles of $Mg^{2+}$ is such that: the lower limit thereof may be, for example, 1:0.0075, 1:0.01, 1:0.075, 1:0.1, or 1:0.2; the upper limit thereof may be, for example, 1:25, 1:20, 1:10, or 1:6; and the range thereof may, for example, from 1:0.0075 to 1:25, from 1:0.0075 to 1:20, from 1:0.1 to 1:10, and or from 1:0.2 to 1:6.

In the second nucleic acid monomer dry reagent, the condition tK of the molar ratio (t:$K^+$) between the total number of moles (t) of all the nucleic acid monomers and the number of moles of $K^+$ is not particularly limited.

The second nucleic acid monomer dry reagent may contain $K^+$ in the form of an ion or salt, for example. Examples of salts of $K^+$ include KCl, $KNO_3$, $K_2SO_4$, KBr, and $K_2CO_3$.

The second nucleic acid monomer dry reagent may further contain, in addition to the nucleic acid monomer, $Mg^{2+}$, and $K^+$, an optional additional component other than the polymerase and the primer. Examples of the optional additional component include a surfactant, a sugar, and a polymer.

Although the second nucleic acid monomer dry reagent may contain Tris, for example, it may not contain Tris. In the case where the second nucleic acid monomer dry reagent contains Tris, the condition sT of the molar ratio (s:Tris) between the at least one type of nucleic acid monomer (s) and the Tris may be, for example, the same as in the first nucleic acid monomer dry reagent. Furthermore, the condition tT of the molar ratio (t:Tris) between the total number of moles (t) of all the nucleic acid monomers and the number of moles of the Tris may be, for example, the same as that in the first nucleic acid monomer dry reagent.

When the second nucleic acid monomer dry reagent contains two or more types of nucleic acid monomers, as described above, the molar ratio (s:Tris) of Tris and the molar ratio (s:$K^+$) of $K^+$ to the at least one type of nucleic acid monomer may satisfy the ranges of the conditions sT and sK, respectively. In some embodiments, the molar ratios of Tris and $K^+$ to each of two types of nucleic acid monomers may satisfy the above ranges, respectively. In additional embodiments, the molar ratios of Tris and $K^+$ to each of three, four, or five types of nucleic acid monomers may satisfy the above ranges, respectively.

The amounts of the nucleic acid monomer, $Mg^{2+}$, $K^+$, and the optional additional component, contained in the second nucleic acid monomer dry reagent are not particularly limited and are, for example, the same as those in the first nucleic acid monomer dry reagent.

When a nucleic acid is amplified, components other than the components contained in the second nucleic acid monomer dry reagent among the above-mentioned "essential components for nucleic acid amplification" may be contained in the above-mentioned polymerase dry reagent (A) and/or primer dry reagent (B), for example.

When a nucleic acid is amplified using the second nucleic acid monomer dry reagent, a reagent to be used in combination with the second nucleic acid monomer dry reagent is not particularly limited, and for example, the polymerase dry reagent (A) and/or primer dry reagent (B) may be used. In the case of using the polymerase dry reagent (A) and/or the primer dry reagent (B) in combination with the second nucleic acid monomer dry reagent, for example, they may be used in the same manner as in the case of using them in combination with the first nucleic acid monomer dry reagent.

A method for producing a second nucleic acid monomer dry reagent is not particularly limited, and for example, it may be produced by drying a second liquid reagent containing the at least one type of nucleic acid monomer, $Mg^{2+}$, and $K^+$.

The second liquid reagent may be prepared according to the types and ratio of components to be contained in the second nucleic acid monomer dry reagent, for example. In the second liquid reagent, the molar ratio (s:$Mg^{2+}$) between the at least one type of nucleic acid monomer (s) and the $Mg^{2+}$ and the molar ratio (s:10 between the at least one type of nucleic acid monomer (s) and the $K^+$ are, for example, the same as mentioned above. Also, the molar ratio between the total number of moles of all the nucleic acid monomers and $Mg^{2+}$ and the molar ratio between the total number of moles of all the nucleic acid monomers and $K^+$ are the same as mentioned above The second liquid reagent may further contain the above-mentioned optional additional component, for example. The second liquid reagent may contain no Tris, for example. In the case where the second liquid reagent contains Tris, the molar ratio (s:Tris) between the nucleic acid monomer (s) and the Tris is the same as mentioned above, for example. Also, the molar ratio between the total number of moles of all the nucleic acid monomers and Tris is the same as mentioned above, for example.

The second liquid reagent may be prepared by dissolving or dispersing the above-mentioned various components in a solvent, for example. The solvent is not particularly limited and may be, for example, water.

A method for amplifying a nucleic acid using the dry reagent of the present invention is not particularly limited, and examples thereof include the PCR method, a reverse transcription (RT)-PCR method, a NASBA (Nucleic acid sequence based amplification) method, a TMA (Transcription-mediated amplification) method, and an SDA (Strand Displacement Amplification) method.

The dry reagent of the present invention also encompasses, as another embodiment, a dry reagent for use in nucleic acid amplification, containing at least one type of nucleic acid monomer and $Mg^{2+}$, wherein the molar ratio between the total number of moles of all the nucleic acid monomers contained in the dry reagent and the number of moles of $Mg^{2+}$ is 1:0.0075 to 1:25. Regarding the details of the dry reagent of the present invention, the above description may be referred to.

The dry reagent kit of the present invention is, as mentioned above, a dry reagent kit for use in nucleic acid amplification, the dry reagent kit including: the dry reagent of the present invention. The dry reagent kit of the present invention is characterized in that it includes the dry reagent of the present invention, and the other configurations and conditions thereof are not at all limited.

In the dry reagent kit of the present invention, any of the first nucleic acid monomer dry reagent and the second nucleic acid monomer dry reagent may be used as the dry reagent of the present invention, for example. The dry reagent kit using the first nucleic acid monomer dry reagent is also referred to as a first dry reagent kit, and the dry reagent kit using the second nucleic acid monomer dry reagent is also referred to as a second dry reagent kit.

The dry reagent kit of the present invention may further include, in addition to the nucleic acid monomer dry reagent of the present invention, the polymerase dry reagent (A) and/or primer dry reagent (B). Specifically, although the dry reagent kit of the present invention may further include, in addition to the nucleic acid monomer dry reagent of the present invention, either one or both of the polymerase dry reagent (A) and the primer dry reagent (B), it may include both of them. The polymerase dry reagent (A) and the primer dry reagent (B) may be prepared in the same manner as in the case of preparing the nucleic acid monomer dry reagent of the present invention, for example.

In the dry reagent kit of the present invention, the dry reagents may be placed in (or on) the respective bases or the same base, for example. In the latter case, the dry reagents may be placed adjacently or may be placed at certain intervals, for example. The placement may be described with reference to the description of the reagent container of the present invention mentioned below, for example. In some embodiments, the dry reagent kit of the present invention may further include instructions for use thereof, for example.

The reagent container of the present invention is, as mentioned above, a reagent container for use in nucleic acid amplification, the reagent container containing: a base; and the dry reagent of the present invention, wherein the dry reagent is placed in (or on) the base. As long as the dry reagent of the present invention is placed in the base of the reagent container of the present invention, the other configurations and conditions of the reagent container are not at all limited.

In the reagent container of the present invention, any of the first nucleic acid monomer dry reagent and the second nucleic acid monomer dry reagent may be used as the dry reagent of the present invention, for example. The reagent container using the first nucleic acid monomer dry reagent is also referred to as a first reagent container, and the reagent container using the second nucleic acid monomer dry reagent is also referred to as a second reagent container.

The reagent container of the present invention may further contain a polymerase dry reagent (A) and/or primer dry reagent (B), for example. Specifically, although either one or both of the polymerase dry reagent (A) and/or the primer dry reagent (B) are placed in the reagent container in addition to the nucleic acid monomer dry reagent, all of the nucleic acid monomer dry reagent, the polymerase dry reagent (A), and the primer dry reagent (B) may be placed therein. In the case where the reagent container of the present invention contains the nucleic acid monomer dry reagent and either one or both of the polymerase dry reagent (A) and the primer dry reagent (B), the dry reagents may be individually placed therein, for example.

In the case where the reagent container of the present invention contains two or more types of the dry reagents as mentioned above, the dry reagents may be individually placed in one reagent region of the base or separately placed in two or more different reagent regions of the base, for example. In the former case, for example, the dry reagents may be dissolved and mixed by introducing a test sample or a solvent in the one reagent region when used. In the latter case, for example, the reagent regions may be connected via flow paths. In this case, for example, the dry reagents may be dissolved and mixed by introducing a test sample or a solvent in any of the reagent regions and thereafter introducing the mixture thus obtained to the other reagent regions via the paths when used. Moreover, the reagent container of the present invention may also be referred to as a reactor because the amplification reaction may be performed in the reagent container of the present invention, for example.

The type of the base is not particularly limited as long as the dry reagent may be placed therein and a nucleic acid amplification reaction may be performed. Examples of the base include a filter paper, a test piece such as a porous body, a tip, a chip and a tube.

The method for producing a dry reagent of the present invention is, as mentioned above, a method for producing a dry reagent for use in nucleic acid amplification, the method including the step of: drying a liquid reagent containing at least one type of nucleic acid monomer and $Mg^{2+}$, wherein the molar ratio between the nucleic acid monomer and the $Mg^{2+}$ in the liquid reagent is from 1:0.03 to 1:100.

For example, in the case where a first nucleic acid monomer dry reagent is produced by the method for producing a dry reagent of the present invention, a first liquid reagent containing at least one type of nucleic acid monomer, $Mg^{2+}$ and containing no $K^+$, with the molar ratio between the nucleic acid monomer and the $Mg^{2+}$ from 1:0.03 to 1:100 may be used as the liquid reagent. For example, in the case where a second nucleic acid monomer dry reagent of the present invention is produced by the method for producing a dry reagent of the present invention, a second liquid reagent containing at least one type of nucleic acid monomer, $Mg^{2+}$, and $K^+$, with the molar ratio between the at least one type of nucleic acid monomer and the $Mg^{2+}$ from 1:0.03 to 1:100 may be used as the liquid reagent. It is to be noted that the method and conditions for preparing the liquid reagent and the method for drying the liquid reagent are the same as mentioned above. In additional embodiments, however, the liquid reagent described herein may also contain a small amount of K as an impurity. In such a case, the condition sK of the molar ratio (s:$K^+$) between the nucleic acid monomer (s) and $K^+$ may have a lower limit including, but not limited to, 1:0.0000001, 1:0.000001, 1:0.00001, 1:0.0001 or 1:0.001; the upper limit including, but not limited to, 1:0.00001, 1:0.0001, 1:0.001, or 1:0.01; and the range thereof may be, for example, from 1:0.0000001 to 1:0.00001, from 1:0.0001 to 1:0.001, from 1:0.0000001 to 1:0.0001, or from 1:0.00001 to 1:0.01.

Still further, the production method of the present invention encompasses, as another embodiment, a production method including the step of drying a liquid reagent containing at least one type of nucleic acid monomer and $Mg^{2+}$, wherein the molar ratio between the total number of moles of all the nucleic acid monomers contained in the liquid reagent and the number of moles of $Mg^{2+}$ is 1:0.0075 to 1:25. Regarding the details of the production method of the present invention, the above description may be referred to.

The dry reagent produced as described above is superior in stability, so that even though it is stored for a long period of time, the quality thereof is the same as before the storage, for example. Thus, the same nucleic acid amplification as in the case of using the dry reagent before the storage may be performed using the dry reagent after the storage in an amount that is the same as the amount of the dry reagent before the storage in the case of using the dry reagent before the storage. The dry reagent produced by the method for producing a dry reagent of the present invention may be stored at 70° C. or less, at about 50° C. (or less) for at least 2 months, at about 30°

C. (or less) for at least 12 months, at 20° C. (or less) for at least 24 months and maintains the same quality as before the storage.

A method for stabilizing a dry reagent of the present invention is a method for stabilizing a dry reagent for use in nucleic acid amplification, the method including the step of: producing a dry reagent by the method for producing a dry reagent of the present invention. The method for stabilizing a dry reagent of the present invention is characterized in that a dry reagent is produced by the method for producing a dry reagent of the present invention, and the other configurations and conditions of the method for stabilizing a dry reagent are not at all limited.

EXAMPLES

The examples of the present invention are described. The present invention, however, is by no means limited thereto. It is to be noted that "%" indicates "w/v %" unless otherwise shown.

In Examples 1A-1B, the storage stability of each of various first nucleic acid monomer dry reagents each containing a nucleic acid monomer and $Mg^{2+}$ and containing no $K^+$ was checked.

Example 1A

In the present example, a nucleic acid monomer and $Mg^{2+}$ as essential components for use in PCR were dried in a container, then the nucleic acid monomer dry reagent thus obtained was stored, and the storage stability thereof was checked.

(1) Preparation of the Dry Reagent

Liquid reagents for drying D1-1 to D1-4 shown in Table 1 were prepared. 2.5 µL each of the liquid reagents for drying were spotted onto the inside of the respective containers and dried overnight at a relative humidity of less than 5% and at 25° C. Thus, dry reagents D1-1 (d0), D1-2 (d0), D1-3 (d0), and D1-4 (d0) were obtained. "d0" indicates a dry reagent which has not been stored as mentioned further below (and hereinafter retains the same meaning).

TABLE 1

| D1-1 | dUTP | 800 µM |
| | d(AUGC)TP | each 800 µM |
| | $(CH_3COO)_2Mg$ | 0 mM |
| D1-2 | dUTP | 800 µM |
| | d(AUGC)TP | each 800 µM |
| | $(CH_3COO)_2Mg$ | 8 µM |
| D1-3 | dUTP | 800 µM |
| | d(AUGC)TP | each 800 µM |
| | $(CH_3COO)_2Mg$ | 800 µM |
| D1-4 | dUTP | 800 µM |
| | d(AUGC)TP | each 800 µM |
| | $(CH_3COO)_2Mg$ | 8 mM |

M: mol/L (2) Storage of the Dry Reagent

The containers containing the respective dry reagents D1-1 (d0) to D1-4 (d0) were sealed, were then placed in the respective plastic bags each containing a drying agent and stored at 50° C. for 17 days and 27 days. The respective dry reagents obtained after storage for 17 days were referred to as dry reagents D1-1 (d17) to D1-4 (d17). The respective dry reagents obtained after storage for 27 days were referred to as dry reagents D1-1 (d27) to D1-4 (d27).

(3) Evaluation of Storage Stability

Nucleic acid amplification using each of the dry reagents obtained after storage for 0, 17, and 27 days was performed by PCR, and then, the storage stability of each of the dry reagents was evaluated.

First, each of the dry reagents was mixed with a liquid reagent prepared just before use. Thus, 10 µL of a PCR reaction solution with the composition shown in Table 2 was prepared. The liquid reagent was prepared so that the final concentrations of the respective components (concentrations of the respective components in the PCR reaction solution) became those shown in Table 2.

TABLE 2

| Amount of reaction solution (10 µl) | |
|---|---|
| Tris-HCl (pH 8.6) | 25 mM |
| KCl | 20 mM |
| $(CH_3COO)_2Mg$ | 2 mM |
| dUTP | 200 µM |
| d(AUGC)P | each 200 µM |
| Probe | 0.2 µM |
| Primer | 1.5 µM |
| BSA | 0.001% |
| Taq polymerase | 0.25 U |
| Purified genome (Roche) | 1 ng |

Primer: Total concentration of forward primer and reverse primer

The probe and primers in Table 2 are as follows.

```
Probe
                                    (SEQ ID NO: 1)
5'-ggagaaggtcaaGgtatc-(BODIPY FL)-3'

Forward primer
                                    (SEQ ID NO: 2)
5'-cggagcccctgcatgcaa-3'

Reverse primer
                                    (SEQ ID NO: 3)
5'-aatgatactatgaatttggggacttcgaa-3'
```

The PCR reaction solution was subjected to PCR using a PCR machine (produced by Eppendorf Co., Ltd.) and then Tm analysis was conducted using a fully-automated SNPs analyzer (trade name: i-densy (registered trademark), produced by ARKRAY, Inc.). PCR was performed as follows. A treatment at 95° C. for 1 minute was performed, and then a cycle of treatment at 95° C. for 10 seconds and at 62° C. for 15 seconds was repeated for a total of 50 cycles. Subsequently, Tm analysis was performed by treating the reaction solution at 95° C. for 1 second, then heating it from 40° C. to 75° C. at a temperature rising rate of 1° C./3 seconds, and measuring the change in fluorescence intensity over time at a wavelength from 520 to 555 nm. Thereafter, the stability of each of the dry reagents was evaluated from the reagent reactivity obtained by the Tm analysis.

The results of the reagent reactivity of the respective dry reagents are shown in Table 3. Table 3 shows the results with respect to the dry reagents D1-1 to D1-4. In Table 3, "$Mg^{2+}$ concentration" indicates the $Mg^{2+}$ concentration in each of the liquid reagents for drying; "Nucleic acid monomer" indicates the types of the nucleic acid monomers present; and "Molar ratio" indicates the molar ratio between each nucleic acid monomer (dATP, dGTP, dCTP, or dUTP) and $Mg^{2+}$ and the molar ratio between the total of all the nucleic acid monomers and $Mg^{2+}$, which means the number of moles of $Mg^{2+}$ relative to the number of moles of each nucleic acid monomer converted to 1 and the number of moles of $Mg^{2+}$ relative to the total number of moles converted to 1, respectively. In each of the three cells of the section denoted "Molar ratio" in respect of each dry reagent, the value in the upper cell is the number of moles of $Mg^{2+}$ relative to dATP, dGTP, or dCTP; the value in the second cell is the number of moles of $Mg^{2+}$ relative to dUTP; and the value in the lower cell is the number of moles of $Mg^{2+}$ relative to the total of all the nucleic acid monomers. The reagent reactivity is represented by the value obtained by dividing the maximum value of "d (fluorescence intensity change amount)/dt" (dF/dt) which is a differential value of the amount of change in fluorescence intensity by the maximum value of the fluorescence value in the Tm analysis.

TABLE 3

| | $Mg^{2+}$ concentration | Nucleic acid monomer | Molar ratio | Reagent reactivity Storage period (day) | | |
|---|---|---|---|---|---|---|
| | | | | 0 d0 | 17 d17 | 27 d27 |
| D1-1 | 0 | d(AGC)TP | — | 9.0 | 4.6 | 0.6 |
| | | dUTP | — | | | |
| | | Total | — | | | |
| D1-2 | 8 µmol/L | d(AGC)TP | 0.01 | 8.6 | 7.1 | 0.6 |
| | | dUTP | 0.005 | | | |
| | | Total | 0.002 | | | |
| D1-3 | 800 µmol/L | d(AGC)TP | 1 | 8.3 | 7.9 | 4.1 |
| | | dUTP | 0.5 | | | |
| | | Total | 0.2 | | | |
| D1-4 | 8 mmol/L | d(AGC)TP | 10 | 7.4 | 8.2 | 8.8 |
| | | dUTP | 5 | | | |
| | | Total | 2 | | | |

The results of the Tm analysis are shown in FIG. 1. FIG. 1 shows graphs of the Tm analysis, each indicating the change in fluorescence intensity accompanying the temperature increase. The horizontal axis indicates the temperature at the time of measurement, and the vertical axis indicates the change in fluorescence intensity. "d (fluorescence intensity change amount)/dt" (dF/dt) which is a differential value of the amount of change in fluorescence intensity was used as the unit. FIG. 1A shows the result obtained using the dry reagent D1-1 (d27). FIG. 1B shows the result obtained using the dry reagent D1-3 (d27). FIG. 1C shows the result obtained using the dry reagent D1-4 (d27).

Figure 1A:
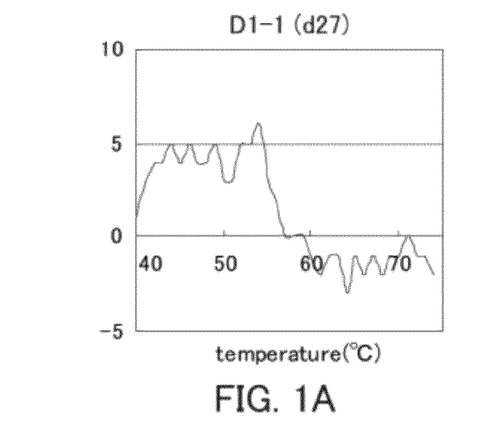
FIG. 1A shows the result obtained using a dry reagent D1-1 (d27).
Figure 1B:
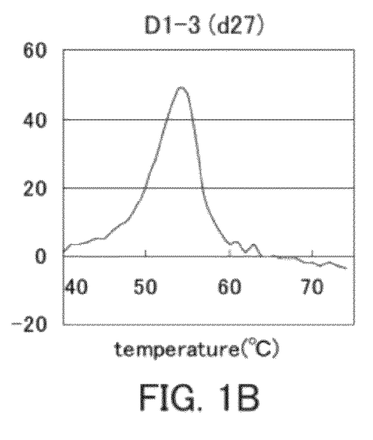
FIG. 1B shows the result obtained using a dry reagent D1-3 (d27).
Figure 1C:
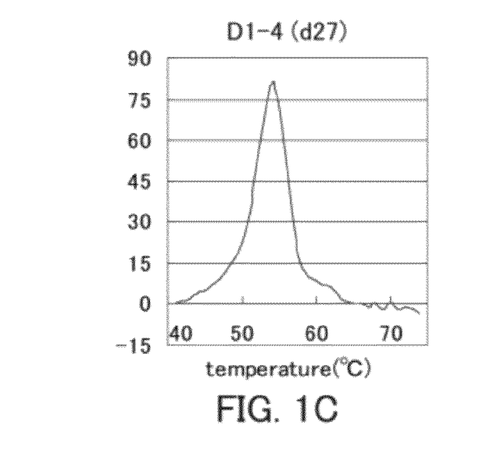
FIG. 1C shows the result obtained using a dry reagent D1-4 (d27).
Figure 1D:
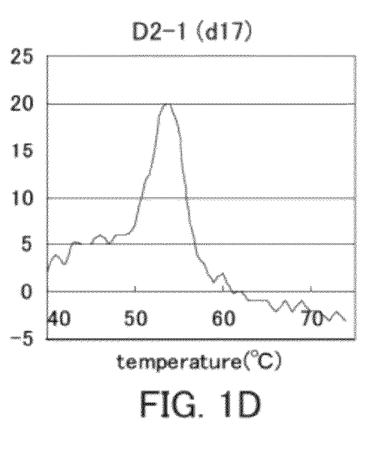
FIG. 1D shows the result obtained using a dry reagent D2-1 (d17).

As mentioned above, the reagent reactivity is represented by the value obtained by dividing the maximum value of "d (fluorescence intensity change amount)/dt" (dF/dt) which is a differential value of the amount of change in fluorescence intensity by the maximum value of the fluorescence value in the Tm analysis. Therefore, there is a correlation between the reagent reactivity and the amount of nucleic acid amplification product obtained by PCR. For example, in the case of the dry reagent D1-1 (d27) with the reagent reactivity of 0.6, a peak was unclear and could not be detected as shown in FIG. 1A. In contrast, in the case of the dry reagent D1-3 (d27) with the reagent reactivity of 4.1 and the dry reagent D1-4 (d27) with the reagent reactivity of 8.8, the respective peaks were clear and could be detected as shown in FIGS. 1B and 1C.

Moreover, there was a tendency for peaks obtained by the Tm analysis to become more clear as the reagent reactivity increased. It may be said from these results that peaks obtained by Tm analysis could not be detected when the reagent reactivity was less than 1, so that nucleic acid amplification could not be performed by the PCR reaction, and peaks obtained by the Tm analysis could be detected when the reagent reactivity was 2 or more, so that nucleic acid amplification could be performed by the PCR reaction, for example.

It was found from the above results that dry reagents each with superior storage stability could be obtained by preparing and drying the liquid reagents with the compositions D1-3 and D1-4 shown in Table 1.

Example 1B

In the present example, Tris was further used as an essential component for use in PCR in addition to a nucleic acid monomer and $Mg^{2+}$, and the influence of Tris on the storage stability of each of various nucleic acid monomer dry reagents was checked.

(1) Preparation of the Dry Reagent

Dry reagents D3-1 (d0) to D3-6 (d0) were prepared in the same manner as in Example 1A except that liquid reagents for drying D3-1 to D3-6 shown in Table 4 were prepared. In the respective dry reagents, the molar ratio between each of dATP, dGTP, and dCTP and $Mg^{2+}$ was 1:10, the molar ratio between dUTP and $Mg^{2+}$ was 1:5, and the molar ratio between all the nucleic acid monomers and $Mg^{2+}$ was 1:2.

TABLE 4

| D3-1 | dUTP | 800 µM |
|---|---|---|
| | d(AUGC)P | each 800 µM |
| | $(CH_3COO)_2Mg$ | 8 mM |
| D3-2 | dUTP | 800 µM |
| | d(AUGC)P | each 800 µM |
| | $(CH_3COO)_2Mg$ | 8 mM |
| | Tris-HCl (pH 8.6) | 1 µM |
| D3-3 | dUTP | 800 µM |
| | d(AUGC)P | each 800 µM |
| | $(CH_3COO)_2Mg$ | 8 mM |
| | Tris-HCl (pH 8.6) | 10 µM |
| D3-4 | dUTP | 800 µM |
| | d(AUGC)P | each 800 µM |
| | $(CH_3COO)_2Mg$ | 8 mM |
| | Tris-HCl (pH 8.6) | 100 µM |
| D3-5 | dUTP | 800 µM |
| | d(AUGC)P | each 800 µM |
| | $(CH_3COO)_2Mg$ | 8 mM |
| | Tris-HCl (pH 8.6) | 1 mM |
| D3-6 | dUTP | 800 µM |
| | d(AUGC)P | each 800 µM |
| | $(CH_3COO)_2Mg$ | 8 mM |
| | Tris-HCl (pH 8.6) | 10 mM |

Then, in the same manner as in Example 1A, the dry reagents were stored and the stability of each of the dry reagents was evaluated. The dry reagents obtained after storage for 17 days were referred to as dry reagents D3-1 (d17) to D3-6 (d17), and the dry reagents obtained after storage for 27 days were referred to as dry reagents D3-1 (d27) to D3-6 (d27).

The results of the reagent reactivity according to Example 1B are shown in Table 5. Table 5 shows the results with respect to the dry reagents D3-1 to D3-6 of Example 1B. In Table 5, "Tris-HCl concentration" indicates the Tris-HCl concentration in each of the liquid reagents for drying; "Nucleic acid monomer" indicates the types of the nucleic acid monomers present; and "Molar ratio" indicates the molar ratio between each nucleic acid monomer (dATP, dGTP, dCTP, or dUTP) and Tris-HCl and the molar ratio between the total of all the nucleic acid monomers and Tris-HCl, which means the number of moles of Tris-HCl relative to the number of moles of each nucleic acid monomer converted to 1 and the number of moles of Tris-HCl relative to the total number of moles converted to 1, respectively. In each three cells of the section denoted "Molar ratio" in respect of each dry reagent, the value in the upper cell is the number of moles of Tris-HCl relative to dATP, dGTP, or dCTP; the value in the second cell is the number of moles of Tris-HCl relative to dUTP; and the value in the lower cell is the number of moles of Tris-HCl relative to the total of all the nucleic acid monomers. In Table 5, the reagent reactivity was calculated in the same manner as in Example 1A.

TABLE 5

| | Tris-HCl concentration | Nucleic acid monomer | Molar ratio | Reagent reactivity Storage period (day) | | |
|---|---|---|---|---|---|---|
| | | | | 0 d0 | 17 d17 | 27 d27 |
| D3-1 | 0 | d(AGC)TP | — | 7.9 | 8.4 | 9.0 |
| | | dUTP | — | | | |
| | | Total | — | | | |
| D3-2 | 1 μmol/L | d(AGC)TP | 0.00125 | 7.8 | 7.7 | 9.2 |
| | | dUTP | 0.000625 | | | |
| | | Total | 0.00025 | | | |
| D3-3 | 10 μmol/L | d(AGC)TP | 0.0125 | 8.5 | 8.7 | 8.5 |
| | | dUTP | 0.00625 | | | |
| | | Total | 0.0025 | | | |
| D3-4 | 100 μmol/L | d(AGC)TP | 0.125 | 8.0 | 8.3 | 8.4 |
| | | dUTP | 0.0625 | | | |
| | | Total | 0.025 | | | |
| D3-5 | 1 mmol/L | d(AGC)TP | 1.25 | 8.5 | 8.7 | 7.9 |
| | | dUTP | 0.625 | | | |
| | | Total | 0.25 | | | |
| D3-6 | 10 mmol/L | d(AGC)TP | 12.5 | 8.8 | 7.9 | 8.7 |
| | | dUTP | 6.25 | | | |
| | | Total | 2.5 | | | |

As shown in Table 5, in the case of using the dry reagents (d27) obtained after storage for 27 days, the reagent reactivity of each of the dry reagents D3-1 (d27) to D3-6 (d27) was 7 or more. Thus, the dry reagents D3-1 (d27) to D3-6 (d27) each exhibited sufficient reactivity. It was found from these results that dry reagents each with superior storage stability could be obtained by preparing and drying the liquid reagents for drying with the compositions D3-1 to D3-6 shown in Table 4.

In Examples 2A to 2C, the storage stability of each of the second nucleic acid monomer dry reagents each containing a nucleic acid monomer, $Mg^{2+}$, and $K^+$ was checked.

Example 2A

In the present example, a nucleic acid monomer, $Mg^{2+}$, and $K^+$ as essential components for use in PCR were dried in a container, then a nucleic acid monomer dry reagent thus obtained was stored, and thereafter the storage stability thereof was checked.

Dry reagents D2-1 (d0) to D2-5 (d0) were obtained in the same manner as in Example 1A except that liquid reagents for drying D2-1 to D2-5 shown in Table 6 were prepared. In the respective dry reagents, the molar ratio between each of dATP, dGTP, and dCTP and $Mg^{2+}$ was 1:10, the molar ratio between dUTP and $Mg^{2+}$ was 1:5, and the molar ratio between all the nucleic acid monomers and $Mg^{2+}$ was 1:2. Furthermore, the molar ratio between each of dATP, dGTP, and dCTP and $K^+$ was 1:100, and the molar ratio between dUTP and $K^+$ was 1:50.

TABLE 6

| D2-1 | dUTP | 800 μM |
|---|---|---|
| | d(AUGC)P | each 800 μM |
| | KCl | 80 mM |
| | $(CH_3COO)_2Mg$ | 0 mM |
| D2-2 | dUTP | 800 μM |
| | d(AUGC)P | each 800 μM |

TABLE 6-continued

| | KCl | 80 mM |
|---|---|---|
| | $(CH_3COO)_2Mg$ | 8 μM |
| D2-3 | dUTP | 800 μM |
| | d(AUGC)P | each 800 μM |
| | KCl | 80 mM |
| | $(CH_3COO)_2Mg$ | 80 μM |
| D2-4 | dUTP | 800 μM |
| | d(AUGC)P | each 800 μM |
| | KCl | 80 mM |
| | $(CH_3COO)_2Mg$ | 800 μM |
| D2-5 | dUTP | 800 μM |
| | d(AUGC)P | each 800 μM |
| | KCl | 80 mM |
| | $(CH_3COO)_2Mg$ | 8 mM |

Then, in the same manner as in Example 1A, the dry reagents were stored and the stability of each of the dry reagents was evaluated. The dry reagents obtained after storage for 17 days were referred to as dry reagents D2-1 (d17) to D2-5 (d17), and the dry reagents obtained after storage for 27 days were referred to as dry reagents D2-1 (d27) to D2-5 (d27).

The results of the reagent reactivity of the respective dry reagents are shown in Table 7. Table 7 shows the results with respect to the dry reagents D2-1 to D2-5. In Table 7, "$Mg^{2+}$ concentration" indicates the $Mg^{2+}$ concentration in each of the liquid reagents for drying; "Nucleic acid monomer" indicates the types of the nucleic acid monomers present; and "Molar ratio" indicates the molar ratio between each nucleic acid monomer (dATP, dGTP, dCTP, or dUTP) and $Mg^{2+}$ and the molar ratio between the total of all the nucleic acid monomers and $Mg^{2+}$, which means the number of moles of $Mg^{2+}$ relative to the number of moles of each nucleic acid monomer converted to 1 and the number of moles of $Mg^{2+}$ relative to the total number of moles converted to 1, respectively. In each three cells of the section of "Molar ratio" in respect of each dry reagent, the value in the upper cell is the number of moles of $Mg^{2+}$ relative to dATP, dGTP, or dCTP; the value in the second cell is the number of moles of $Mg^{2+}$ relative to dUTP; and the value in the lower cell is the number of moles of $Mg^{2+}$ relative to the total of all the nucleic acid monomers. In Table 7, the reagent reactivity was calculated in the same manner as in Example 1A.

TABLE 7

| | $Mg^{2+}$ concentration | Nucleic acid monomer | Molar ratio | Reagent reactivity Storage period (day) | | |
|---|---|---|---|---|---|---|
| | | | | 0 d0 | 17 d17 | 27 d27 |
| D2-1 | 0 | d(AGC)TP | — | 9.3 | 2.1 | 0.5 |
| | | dUTP | — | | | |
| | | Total | — | | | |
| D2-2 | 8 μmol/L | d(AGC)TP | 0.01 | 8.0 | 5.7 | 0.6 |
| | | dUTP | 0.005 | | | |
| | | Total | 0.002 | | | |
| D2-3 | 80 μmol/L | d(AGC)TP | 0.1 | 7.8 | 6.5 | 4.1 |
| | | dUTP | 0.05 | | | |
| | | Total | 0.02 | | | |
| D2-4 | 800 μmol/L | d(AGC)TP | 1 | 8.3 | 6.4 | 8.0 |
| | | dUTP | 0.5 | | | |
| | | Total | 0.2 | | | |
| D2-5 | 8 mmol/L | d(AGC)TP | 10 | 7.8 | 8.3 | 6.9 |
| | | dUTP | 5 | | | |
| | | Total | 2 | | | |

As shown in Table 7, in the case of using the dry reagents (d27) obtained after storage for 27 days, the reagent reactivity of each of the dry reagents D2-3 (d27) to D2-5 (d27) was 4 or more. In contrast, the reagent reactivity of each of the dry reagents D2-1 (d27) and D2-2 (d27) was less than 1.

The results of the Tm analysis are shown in FIG. 1. FIG. 1 shows graphs of the Tm analysis, each indicating the change in fluorescence intensity accompanying the temperature increase. The horizontal axis indicates the temperature at the time of measurement, and the vertical axis indicates the change in fluorescence intensity. "d (fluorescence intensity change amount)/dt" (dF/dt) which is a differential value of the amount of change in fluorescence intensity was used as the unit. FIG. 1D shows the result obtained using the dry reagent D2-1 (d17). FIG. 1E shows the result obtained using the dry reagent D2-1 (d27). FIG. 1F shows the result obtained using the dry reagent D2-5 (d27).

Figure 1E:
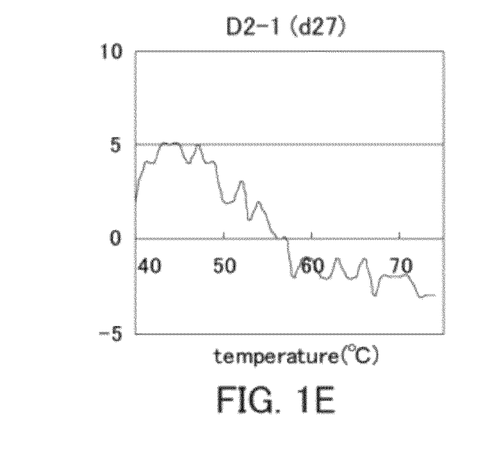
FIG. 1E shows the result obtained using a dry reagent D2-1 (d27).
Figure 1F:
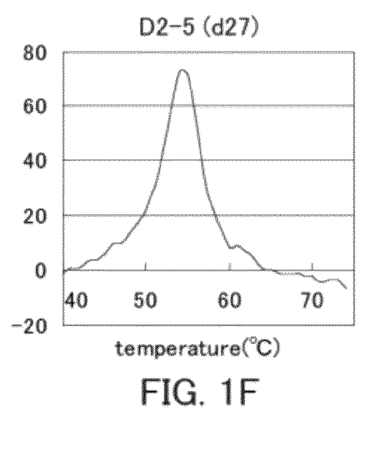
FIG. 1F shows the result obtained using a dry reagent D2-5 (d27).

As mentioned above, the reagent reactivity is represented by the value obtained by dividing the maximum value of "d (fluorescence intensity change amount)/dt" (dF/dt) which is a differential value of the amount of change in fluorescence intensity by the maximum value of the fluorescence value in the Tm analysis. Therefore, there is a correlation between the reagent reactivity and the amount of nucleic acid amplification product obtained by PCR. The dry reagent D2-1 (d27) exhibited a reagent reactivity of 2.1 when the storage period was 17 days, and the peak was clear and could be detected as shown in FIG. 1C. However, the dry reagent D2-1 (d27) exhibited a reagent reactivity of 0.5 when the storage period was 27 days, and a peak was unclear and could not be detected. In contrast, in the case of the dry reagent D2-5 (d27) with a reagent reactivity of 6.9, the peak was clear and could be detected as shown in FIG. 1E, even when the storage period was 27 days.

It was found from the above results that dry reagents each with superior storage stability could be obtained by preparing and drying the liquid reagents with the compositions D2-3 to D2-5 shown in Table 6.

Example 2B

In the present example, Tris was further used as an essential component for use in PCR in addition to a nucleic acid monomer, $Mg^{2+}$, and $K^+$, and the influence of Tris on the storage stability of each the nucleic acid monomer dry reagents was checked.

(1) Preparation of the Dry Reagent

Dry reagents D4-1 (d0) to D4-6 (d0) were prepared in the same manner as in Example 1A except that liquid reagents for drying D4-1 to D4-6 shown in Table 8 were prepared. In the respective dry reagents, the molar ratio between each of dATP, dGTP, and dCTP and $Mg^{2+}$ was 1:10, the molar ratio between dUTP and $Mg^{2+}$ was 1:5, and the molar ratio between all the nucleic acid monomers and $Mg^{2+}$ was 1:2. Furthermore, the molar ratio between each of dATP, dGTP, and dCTP and $K^+$ was 1:100, and the molar ratio between dUTP and $K^+$ was 1:50.

TABLE 8

| | | |
|---|---|---|
| D4-1 | dUTP | 800 μM |
| | d(AUGC)P | each 800 μM |
| | KCl | 80 mM |
| | $(CH_3COO)_2Mg$ | 8 mM |
| D4-2 | dUTP | 800 μM |
| | d(AUGC)P | each 800 μM |
| | KCl | 80 mM |
| | $(CH_3COO)_2Mg$ | 8 mM |
| | Tris-HCl (pH 8.6) | 1 μM |
| D4-3 | dUTP | 800 μM |
| | d(AUGC)P | each 800 μM |

TABLE 8-continued

| | | |
|---|---|---|
| | KCl | 80 mM |
| | $(CH_3COO)_2Mg$ | 8 mM |
| | Tris-HCl (pH 8.6) | 10 μM |
| D4-4 | dUTP | 800 μM |
| | d(AUGC)P | each 800 μM |
| | KCl | 80 mM |
| | $(CH_3COO)_2Mg$ | 8 mM |
| | Tris-HCl (pH 8.6) | 100 μM |
| D4-5 | dUTP | 800 μM |
| | d(AUGC)P | each 800 μM |
| | KCl | 80 mM |
| | $(CH_3COO)_2Mg$ | 8 mM |
| | Tris-HCl (pH 8.6) | 1 mM |
| D4-6 | dUTP | 800 μM |
| | d(AUGC)P | each 800 μM |
| | KCl | 80 mM |
| | $(CH_3COO)_2Mg$ | 8 mM |
| | Tris-HCl (pH 8.6) | 10 mM |

Then, in the same manner as in Example 1A, the dry reagents were stored, and the stability of each of the dry reagents was evaluated. The dry reagents obtained after storage for 17 days were referred to as dry reagents D4-1 (dl 7) to D4-6 (dl 7), and the dry reagents obtained after storage for 27 days were referred to as dry reagents D4-1 (d27) to D4-6 (d27).

The results of the reagent reactivity according to Example 2B are shown in Table 9. Table 9 shows the results with respect to the dry reagents D4-1 to D4-6 of Example 2B. In Table 9, "Tris-HCl concentration" indicates the Tris-HCl concentration in each of the liquid reagents for drying; "Nucleic acid monomer" indicates the types of the nucleic acid monomers present; and "Molar ratio" indicates the molar ratio between each nucleic acid monomer (dATP, dGTP, dCTP, or dUTP) and Tris-HCl and the molar ratio between the total of all the nucleic acid monomers and Tris-HCl, which means the number of moles of Tris-HCl relative to the number of moles of each nucleic acid monomer converted to 1 and the number of moles of Tris-HCl relative to the total number of moles converted to 1, respectively. In each three cells of the section denoted "Molar ratio" in respect of each dry reagent, the value in the upper cell is the number of moles of Tris-HCl relative to dATP, dGTP, or dCTP; the value in the second cell is the number of moles of Tris-HCl relative to dUTP; and the value in the lower cell is the number of moles of Tris-HCl relative to the total of all the nucleic acid monomers. In Table 9, the reagent reactivity was calculated in the same manner as in Example 1A.

TABLE 9

| | | | | Reagent reactivity Storage period (day) | | |
|---|---|---|---|---|---|---|
| | Tris-HCl concentration | Nucleic acid monomer | Molar ratio | 0 d0 | 17 d17 | 27 d27 |
| D4-1 | 0 | d(AGC)TP | — | 9.2 | 8.7 | 8.8 |
| | | dUTP | — | | | |
| | | Total | — | | | |
| D4-2 | 1 μmol/L | d(AGC)TP | 0.00125 | 8.7 | 9.0 | 7.8 |
| | | dUTP | 0.000625 | | | |
| | | Total | 0.00025 | | | |
| D4-3 | 10 μmol/L | d(AGC)TP | 0.0125 | 8.8 | 9.0 | 9.2 |
| | | dUTP | 0.00625 | | | |
| | | Total | 0.0025 | | | |
| D4-4 | 100 μmol/L | d(AGC)TP | 0.125 | 7.8 | 7.6 | 8.8 |
| | | dUTP | 0.0625 | | | |
| | | Total | 0.025 | | | |

TABLE 9-continued

|  | Tris-HCl concentration | Nucleic acid monomer | Molar ratio | Reagent reactivity Storage period (day) | | |
|---|---|---|---|---|---|---|
|  |  |  |  | 0 d0 | 17 d17 | 27 d27 |
| D4-5 | 1 mmol/L | d(AGC)TP dUTP Total | 1.25 0.625 0.25 | 8.2 | 8.2 | 9.3 |
| D4-6 | 10 mmol/L | d(AGC)TP dUTP Total | 12.5 6.25 2.5 | 8.6 | 8.6 | 8.3 |

As shown in Table 9, in the case of using the dry reagents (d27) obtained after storage for 27 days, the reagent reactivity of each of the dry reagents D4-1 (d27) to D4-6 (d27) was 7 or more. Thus, the dry reagents D4-1 (d27) to D4-6 (d27) each exhibited sufficient reactivity. It was found from these results that dry reagents each with superior storage stability could be obtained by preparing and drying the liquid reagents with the compositions D4-1 to D4-6 shown in Table 8.

Example 2C

In the present example, components for use in PCR were divided into three groups, which were then dried in the respective containers, thereafter three types of dry reagents thus obtained were stored, and then the storage stability of each of the dry reagents was checked.

(1) Preparation of Each Dry Reagent

Dry reagents D5 to D7 were obtained in the same manner as in Example 1A except that liquid reagents for drying D5 to D7 shown in Table 10 were prepared. The polymerase in D6 and primers and a probe in D7 were the same as those used in Example 1A.

TABLE 10

| D5 | |
|---|---|
| KCl | 80 mM |
| dUTP | 800 μM |
| d(AUGC)TP | each 800 μM |
| MgCl$_2$ | 8 mM |
| D6 | |
| 20% BSA | 0.2% |
| Taq polymerase | 1.5 U |
| UNG (dialyzed) | 0.2 U |
| D7 | |
| Tris-HCl (pH 8.6) | 100 mM |
| Probe | 0.8 μM |
| Primer | 6 μM |

Primer: Total concentration of forward primer and reverse primer (2) Storage of the Dry Reagent The containers containing the respective dry reagents were sealed, were then placed in the respective plastic bags each containing a drying agent and stored at 30° C. and 50° C. for 30, 60, 240, and 370 days.

(3) Evaluation of Storage Stability

Nucleic acid amplification using each of the dry reagents D5 to D7 obtained after storage for 0, 30, 60, 240, and 370 days was performed by PCR. Then the storage stability of each of the dry reagents was evaluated. The dry reagents D5 to D7 obtained after storage for the same number of days were used in combination.

10 μL (30 pg/μL) of purified human-derived nucleic acid was added to a container containing the dry reagent D5, and the purified nucleic acid and the dry reagent D5 were mixed with each other. Then the mixture thus obtained was added to a container containing the dry reagent D6, and the mixture and the dry reagent D6 were mixed with each other. Thereafter, the mixture thus obtained was added to a container containing the dry reagent D7, and the mixture and the dry reagent D7 were mixed with each other. As described above, the purified nucleic acid, as a template nucleic, acid and the dry reagents D5, D6, and D7, were mixed. The resultant mixture, as a PCR reaction solution, was subjected to PCR and Tm analysis. PCR and Tm analysis were performed in the same manner as in Example 1A except that the PCR was performed as follows. A treatment at 95° C. for 1 minute was conducted, and then a cycle of treatment at 95° C. for 1 second and at 60° C. for 15 seconds was repeated for a total of 50 cycles.

The results of the reagent reactivity according to the present example are shown in Table 11. In Table 11, the reagent reactivity was calculated in the same manner as in Example 1A.

TABLE 11

|  | Reagent reactivity Storage temperature (° C.) | |
|---|---|---|
| Storage period (day) | 30 | 50 |
| 0 | 10.3 | 10.3 |
| 30 | 9.5 | 5.6 |
| 60 | 8.3 | 2.0 |
| 240 | 7.6 | —* |
| 370 | 7.2 | —* |

*Not measured

As shown in Table 11, the reagent reactivity of each of the dry reagents obtained after storage at 30° C. was 7 or more even after being stored for 370 days. Moreover, the reagent reactivity of the dry reagent obtained after storage at 50° C. for 60 days was 2, which proves that a peak may be detected. It was found from these results that dry reagents D5, D6, and D7 which may be stably stored at 30° C. for at least 12 months and at 50° C. for at least 2 months, may be obtained by preparing and drying the liquid reagents with the compositions shown in Table 10.

Comparative Example 1

In the present example, some of components for use in PCR were dried in the respective containers, then the dry reagents thus obtained were stored, and thereafter the storage stability of each of the dry reagents was checked.

(1) Preparation of the Dry Reagent

Dry reagents D8 and D9 shown in Table 12 were obtained in the same manner as in Example 1A except that liquid reagents for drying D8 and D9 shown in Table 12 were prepared and dried overnight at a relative humidity of less than 10% and 25° C. It is to be noted that $Mg^{2+}$ was not added to the liquid reagent for drying D8, and the liquid reagent for drying D9 had the same composition as the liquid reagent for drying D4-8 of Example 2B. The primers and probe in the liquid reagent for drying D8 were the same as those used in Example 1A.

TABLE 12

| D8 | |
|---|---|
| dUTP | 0.2 mM |
| d(AUGC)P | 0.2 mM |
| Tris-HCl (pH 8.6) | 25 mM |
| KCl | 20 mM |
| Probe | 0.2 µM |
| Primer | Total: 1.5 µM |

| D9 | |
|---|---|
| dUTP | 0.2 mM |
| d(AUGC)P | 0.2 mM |
| Tris-HCl (pH 8.6) | 25 mM |
| KCl | 20 mM |
| $(CH_3COO)_2Mg$ | 2 mM |

Primer: Total concentration of forward primer and reverse primer (2) Storage of the Dry Reagent The containers containing the respective dry reagents were sealed, were then placed in the respective plastic bags each containing a drying agent and stored at 50° C. for 14 days. The dry reagents obtained after storage for 0 day were referred to as dry reagents D8 (d0) and D9 (d0), and the dry reagents obtained after storage for 14 days were referred to as dry reagents D8 (d14) and D9 (d14).

(3) Evaluation of Storage Stability

Nucleic acid amplification using each of the dry reagents D8 and D9 obtained after storage for 0 and 14 days was performed by PCR. Then the storage stability of each of the dry reagents was evaluated.

A liquid reagent for dry reagent D8 with the composition shown in Table 13 and 1 µL of human genome (100 copies/µL) were added to a container containing the dry reagent D8. Thus, a total of 10 µL of a PCR reaction solution was prepared. Then the PCR reaction solution was subjected to PCR and Tm analysis in the same manner as in Example 1A. Moreover, a liquid reagent for dry reagent D9 with the composition shown in Table 13 and 1 µL of human genome (100 copies/µL) were added to a container containing the dry reagent D9. Thus, a total of 10 µL of a PCR reaction solution was prepared. Then the PCR reaction solution was subjected to PCR and Tm analysis in the same manner as in Example 1A. In Table 13, the concentration of each component represents the final concentration thereof in 10 µL of each PCR reaction solution.

TABLE 13

| Liquid reagent for dry reagent D8 | |
|---|---|
| $(CH_3COO)_2Mg$ | 2 mM |
| BSA | 0.10% |
| Gene Taq FP | 0.25 U |

| Liquid reagent for dry reagent D9 | |
|---|---|
| $(CH_3COO)_2Mg$ | 2 mM |
| BSA | 0.10% |
| Gene Taq FP | 0.25 U |
| Probe | 0.2 µM |
| Primer | 1.5 µM |

Primer: Total concentration of forward primer and reverse primer
Gene Taq FP: Polymerase, produced by Nippon Gene Co., Ltd.

The results of the reagent reactivity according to the present comparative example are shown in Table 14. In Table 14, the reagent reactivity was calculated in the same manner as in Example 1A.

TABLE 14

| | Reagent reactivity Storage period (day) | |
|---|---|---|
| | 0<br>d 0 | 14<br>d 14 |
| D 8 | 9.6 | 0.6 |
| D 9 | 4.2 | 0.8 |

As shown in Table 14, when the dry reagents D8 and D9 were stored at 50° C. for 14 days, the reagent reactivity was less than 1. Thus it was found that the dry reagents D8 and D9 were dry reagents each with low storage stability.

According to the dry reagent of the present invention, a nucleic acid may be amplified even after storing the dry reagent at room temperature, for example. Therefore, for example, the handling of the dry reagent becomes really easy when a large number of test samples are subjected to nucleic acid amplifications, and the dry reagents are distributed. Moreover, the dry reagent may be stored in a dry state. Therefore, for example, it becomes possible to make a chip by placing all of the essential components on a chip. As described above, the dry reagent of the present invention may maintain the ability to amplify a nucleic acid even after being stored, and the handling of the dry reagent is improved. Thus, it may be said that the dry reagent of the present invention is a really useful tool in gene analysis utilizing nucleic acid amplification and the like.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all variations which come within the meaning and range of equivalency of the claims are intended to be embraced therein.

The invention claimed is:

1. A dry reagent kit for use in nucleic acid amplification, the dry reagent kit comprising:
   a first dry reagent comprising at least one type of nucleic acid monomer, tris(hydroxymethyl)aminomethane, and $Mg^{2+}$, wherein a molar ratio of the at least one type of nucleic acid monomer to the $Mg^{2+}$ is from 100/3 to 1/100 and/or a molar ratio of the total number of moles of all the nucleic acid monomers contained in the dry reagent to the number of moles of the $Mg^{2+}$ is from 10000/75 to 1/25;
   a second dry reagent comprising polymerase but not $Mg^{2+}$, $K^+$, tris(hydroxymethyl)aminomethane, a nucleic acid monomer, or a primer; and
   a third dry reagent comprising a primer but not $K^+$,
   wherein the first, second, and third dry reagents are not mixed with one another.

2. The dry reagent kit according to claim 1, wherein the molar ratio of the at least one type of nucleic acid monomer to the $Mg^{2+}$ in the first dry reagent is from 100/3 to 1/50.

3. The dry reagent kit according to claim 1, wherein the molar ratio of the at least one type of nucleic acid monomer to the $Mg^{2+}$ in the first dry reagent is from 1 to 1/30.

4. The dry reagent kit according to claim 1, wherein the molar ratio of the at least one type of nucleic acid monomer to the tris(hydroxymethyl)aminomethane is 1/60 or more 1:60 or less.

5. The dry reagent kit according to claim 4, wherein the molar ratio of the at least one type of nucleic acid monomer to and the tris(hydroxymethyl)aminomethane is 1/30 or more.

6. The dry reagent kit according to claim 1, wherein the first dry reagent comprises, as the at least one type of nucleic acid monomer, a nucleic acid monomer having adenine, a nucleic acid monomer having guanine, a nucleic acid monomer having cytosine, and a nucleic acid monomer having thymine, and each of the nucleic acid monomers satisfies the molar ratio(s).

7. The dry reagent kit according to claim 1, wherein the first dry reagent comprises, as the at least one type of nucleic acid monomer, a nucleic acid monomer having adenine, a nucleic acid monomer having guanine, a nucleic acid monomer having cytosine, and a nucleic acid monomer having uracil,
the nucleic acid monomer having adenine, the nucleic acid monomer having guanine, and the nucleic acid monomer having cytosine each satisfy the molar ratio, and
the ratio of the average number of moles calculated from the numbers of moles of the nucleic acid monomer having adenine, the nucleic acid monomer having guanine, and the nucleic acid monomer having cytosine to the number of moles of the nucleic acid monomer having uracil is from 10/5 to 1/10.

8. The dry reagent kit according to claim 1, wherein the molar ratio of the total number of moles of all the nucleic acid monomers contained in the first dry reagent to the number of moles of $Mg^{2+}$ is from 10000/75 to 1/25.

9. The dry reagent kit according to claim 1, wherein the molar ratio of the at least one type of nucleic acid monomer to the $Mg^{2+}$ in the first dry reagent is from 10/3 to 1/100, and the dry reagent does not comprise K.

10. The dry reagent kit according to claim 1, wherein the first dry reagent further comprises $K^+$.

11. The dry reagent kit according to claim 10, wherein a molar ratio of the at least one type of nucleic acid monomer to $K^+$ in the first dry reagent is from 100/1 to 1/1000.

12. A reagent container configured for use in nucleic acid amplification, the reagent container comprising:
   a base, wherein the base is a test piece, a chip, or a tube; and
   the dry reagent kit according to claim 1, wherein the dry reagent is placed in the base.

* * * * *